United States Patent [19]

Hichens et al.

[11] Patent Number: 5,206,260
[45] Date of Patent: Apr. 27, 1993

[54] HEXAHYDROPYRROLO[2,3-B]INDOLE DERIVATIVES

[75] Inventors: Martin Hichens, Lansdale; Hanumath G. P. Kari, Hatfield; Kamlesh P. Vyas, Harleysville, all of Pa.

[73] Assignee: Merck & Co., Inc., Rahway, N.J.

[21] Appl. No.: 789,223

[22] Filed: Nov. 7, 1991

[51] Int. Cl.$^5$ .................. C07D 487/04; A61K 31/405
[52] U.S. Cl. ...................... 514/411; 548/429
[58] Field of Search .......... 548/429; 514/411

[56] References Cited

U.S. PATENT DOCUMENTS

| | | | |
|---|---|---|---|
| 4,765,985 | 8/1988 | Leeson | 548/429 |
| 4,791,107 | 12/1988 | Hamer et al. | 548/429 |
| 4,831,155 | 5/1989 | Brufani et al. | 548/429 |
| 4,900,748 | 2/1990 | Brossi et al. | 514/411 |
| 4,978,673 | 12/1990 | Meroni et al. | 514/411 |

FOREIGN PATENT DOCUMENTS 2005259  4/1979  United Kingdom .

OTHER PUBLICATIONS

Drugs of the Future, 1991 16(1), pp. 33–36.
Stern et al., Ann. Neurol. 22: 306–310 (1987).
Unni, et al. (I), Eur. J. Clin. Pharmacol, 41: 83–84 )1991).
Somani, Biopharm. Drug Dispo., 10, 187–203 (1989).
Giacobini, et al. Neuropharm., 26, 831–836 (1987).
Somani, et al., Drug Metab. Dispo., 15, 627–633 (1987).
Unni, et al., (II), Drug Metab. Dispo., 14, 183–189 (1986).
Isaksson et al., J. Chromatog., 419, 165–175 (1987).

Primary Examiner—Mary C. Lee
Assistant Examiner—Mary Susan H. Gabilan

[57] ABSTRACT

Mammalian metabilites of the known acetylchloinesterase inhibitor trimethyl-1,3a,8-hexahydro-1,2,3,3a,8,8a-pyrrol[2,3-b]indole-5(3aS,8aR) heptylcarbamate are themselves cholinesterase inhibitors useful in the treatment of various memory dysfunctions characterized by a cholinergic deficit such as Alzheimer's disease and are also useful as analgesic agents in the alleviation of pain.

15 Claims, No Drawings

HEXAHYDROPYRROLO[2,3-B]INDOLE DERIVATIVES

SUMMARY OF THE INVENTION

The present invention is related to compounds of the general structural Formula I:

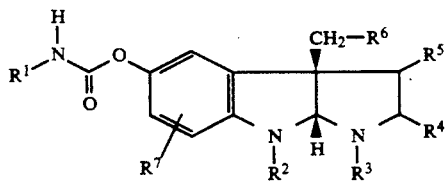

wherein $R^1$, $R^2$, $R^3$, $R^4$, $R^5$, $R^6$ and $R^7$ are hereinafter defined. These compounds were first discovered as mammalian metabolites of the acetylcholinesterase inhibitor trimethyl-1,3a,8-hexahydro-1,2,3,3a,8,8a-pyrrol[2,3-b]indole-5(3aS,8aR) heptylcarbamate which has the structural formula:

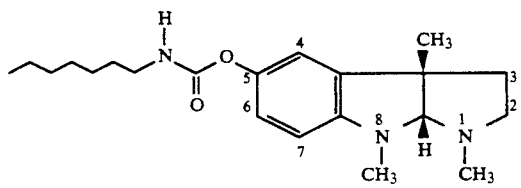

and which is specifically described in U.S. Pat. No. 4,831,155.

This invention also relates to processes for the preparation of the novel compounds, pharmaceutical compositions thereof, a method of alleviating pain and a method of treating various memory dysfunctions characterized by a cholinergic deficit.

BACKGROUND OF THE INVENTION

The cholinergic neuronal system can be found in the central nervous system (CNS), in the autonomic nervous sytem, and in the skeletal motor system. Acetylcholine (ACh) is the neurotransmitter in all ganglia, the neuromuscular junction, and the post-ganglionic synapses of the cholinergic nervous system. Acetylcholine is normally an excitatory neurotransmitter that binds to nicotinic and muscarinic receptors.

In particular, acetylcholinesterase (AChE) is an enzyme that hydrolyzes and thereby deactivates ACh after it binds to a receptor. This enzyme is present in all peripheral and central junctional sites and in certain cells of the body. Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus.

In some circumstances, it is desirable to stimulate acetylcholine receptors. One method involves the use of indirect agonists, such as anticholinesterase drugs, which inhibit the hydrolysis of ACh by AChE. When an anticholinesterase drug blocks AChE and inhibits the destruction of released ACh, a higher neurotransmitter level and increased biological response result. For example, the alkaloid physostigmine, trimethyl-1,3a,8-hexahydro-1,2,3,3a,8,8a-pyrrol[2,3-b]indole-5(3aS,-8aR)methylcarbamate, which can be isolated from the seeds of the Calabar bean, has been found to be an anticholinesterase drug.

Alzheimer's disease is a neurodegenerative disease of the brain leading to severely impaired cognition and functionality, in which there is a significant loss of the cerebral cortex acetylcholine concentration. It is believed that degeneration of the cholinergic pathways in the CNS may be a principal cause of dementia of the Alzheimer's type. This disease leads to progressive regression of memory and learned functions. Since the average age of the population is on the increase, the frequency of Alzheimer's disease is increasing and requires urgent attention.

Cholinesterases are found throughout the body, both in the brain and in blood serum. However, only brain acetylcholinesterase (AChE) distribution is correlated with central cholinergic innervation. This same innervation is suggested to be weakened in Alzheimer patients.

It has been suggested that cholinergic agonists, such as the anticholinesterase drugs, are useful in the treatment of Alzheimer's disease. In particular, physostigmine (eserine), being an inhibitor of acetylcholinesterase, has been used in its treatment. The administration of physostigmine has the drawback of being considerably limited by its short half-life of effect, poor oral bioavailability, and severe dose-limiting side-effects, particularly towards the digestive system. Thus, there is a need in the art for new forms of drugs for the treatment of this disease.

The enantiomers of physostigmine and pharmaceutically active physostigmine-like compounds, such as the compounds described in U.S. Pat. Nos. 4,791,107, 4,831,155, 4,900,748, 4,914,102 or 4,971,992, are under investigation for the treatment of Alzheimer's disease.

The pharmacokinetics and pharmacodynamics of physostigmine upon oral and intravenous administration to a mammal have been examined (see for example Somani, et al., Biopharm. Drug Dispo., 10, 187–203 (1989); Giacobini, et al., Neuropharm., 26, 831–836 (1987); Somani, et al., Drug Metab. Dispo., 15, 627–633 (1987); Somani, et al., Fund. Appl. Toxicol., 6, 327–334 (1986); Unni, et al., Drug Metab. Dispo., 14, 183–189 (1986); Boyer, et al., Arch. int. Pharmacodyn., 278 180–192 (1985); Somani, et al., Eur. J. Drug Metab. Pharmacokin., 10, 343–349 (1985); Hemsworth, et al., J. Pharm. Sci., 59, 118–120 (1970)). The metabolism of physostigmine upon incubation with mouse liver microsomes has also been examined (Isaksson, et al., J. Chromatog., 419, 165–175 (1987)). In particular, it has been reported that physostigmine is metabolized to eseroline and at least three other unknown metabolites (Somani, et al., Biopharm. Drug Dispo., 10, 187–203 (1989)). Mammalian metabolites of heptylphysostigmine, trimethyl-1,3a-8-hexahydro-1,2,3,3a,8,8a-pyrrol[2,3-b]indole-5(3aS,8aR)heptylcarbamate, however, have not been previously reported.

Accordingly, with the present invention there are provided derivatives of physostigmine which have cholinesterase inhibitory activity.

DETAILED DESCRIPTION OF THE INVENTION

A. Scope of the Invention

The novel compound of this invention has structural Formula I:

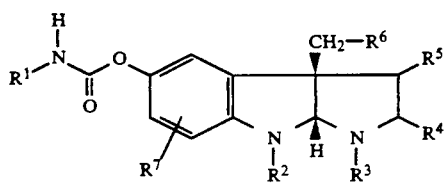

or a pharmaceutically acceptable salt thereof, wherein:

$R^1$ is selected from the group consisting of:
(1) —$(CH_2)_6CH_3$,
(2) —$C_7H_{14}OH$,
(3) —$(CH_2)_4$—$CO_2H$, and
(4) —$(CH_2)_2$—$CO_2H$;

$R^2$ is hydrogen or —$CH_2R^8$;
$R^3$ is hydrogen or —$CH_2R^9$;
$R^4$, $R^5$, $R^6$, $R^7$, $R^8$ and $R^9$ are independently selected from: hydrogen and hydroxy;
with the proviso that if $R^2$ is —$CH_2R^8$, $R^3$ is —$CH_2R^9$, and $R^4$, $R^5$, $R^6$, $R^7$, $R^8$ and $R^9$ are hydrogen, then $R^1$ is other than —$(CH_2)_6CH_3$.

B. Preparation of Compounds within the Scope of the Present Invention

The compounds of the present invention are prepared from metabolism by a mammalian species of the compound trimethyl-1,3a,8-hexahydro-1,2,3,3a,8,8a-pyrrol[2,3-b]indole-5(3aS,8aR)heptylcarbamate following therapeutic administration such as by oral or intravenous administration, or by incubation with mammalian liver microsomes in the presence of $MgCl_2$ and NADPH in a buffer of approximately neutral pH and at approximately 30°–40° C. Alternatively, the compounds of the present invention may be prepared by utilizing the synthetic schemes described herein.

In particular, the following compounds were discovered among the mammalian metabolites of trimethyl-1,3a,8-hexahydro-1,2,3,3a,8,8a-pyrrol[2,3-b]indole-5(3aS,8aR)heptylcarbamate:

Metabolite 1

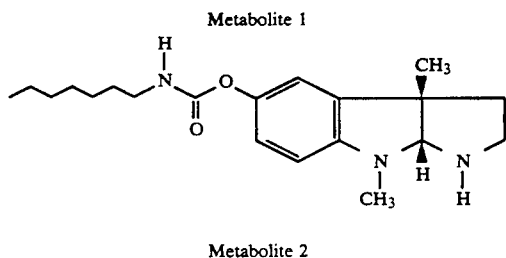

Metabolite 2

Metabolite 3

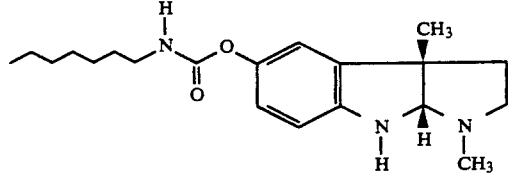

Metabolite 4

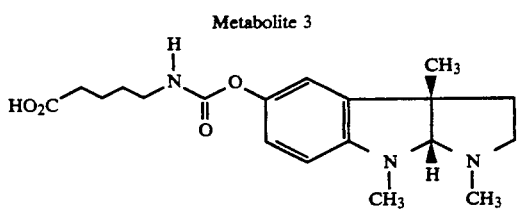

Metabolite 5

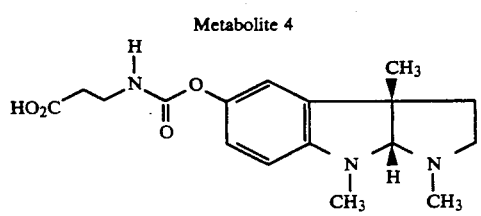

Metabolite 6

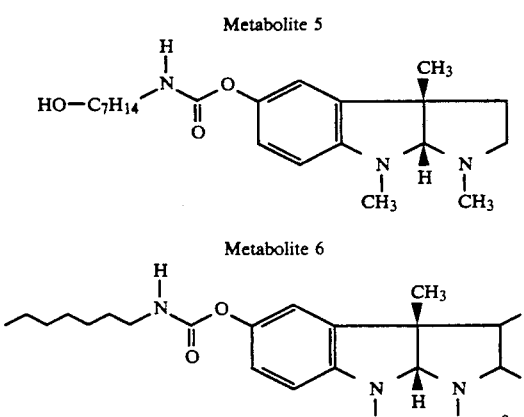

(wherein one of $R^4$, $R^5$ and $R^9$ is hydroxy, and the remaining two are hydrogen)

Metabolite 7

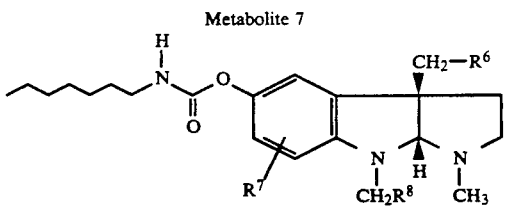

(wherein one of $R^6$, $R^7$ and $R^8$ is hydroxy and the remainig two are hydrogen).

The compounds eseroline and eseroline glucuronide were also discovered among the mammalian metabolites of trimethyl-1,3a,8-hexahydro-1,2,3,3a,8a-pyrrol[2,3-b]indole-5(3aS,8aR)heptylcarbamate.

The foregoing metabolites were originally isolated from dog urine following oral dosing with trimethyl-1,3a,8-hexahydro-1,2,3,3a,8,8a-pyrrol-[2,3-b]indole-5(3aS,8aR)heptylcarbamate at dosage levels of 1 mg/kg/day. Some of these compounds were also isolated from an incubation mixture of canine liver microsomes and trimethyl-1,3a,8-hexahydro-1,2,3,3a,8,8a-pyrrol[2,3-b]indole-5(3aS,8aR)-heptylcarbamate at a concentration of 10 μM in the presence of MgCl₂ and NADPH in a buffer of approximately neutral pH at approximately 30°–40° C. The compounds were isolated from the biological matrix by selective solid phase or solvent extraction and purified by liquid chromatography (LC) using different mobile phase conditions. The procedures and the results of these experiments are noted in Examples 1–3.

These compounds and others within Formula I may be prepared by modification of synthetic sequences described in U.S. Pat. Nos. 4,791,107, 4,831,155 and 4,978,673 or by the following schemes wherein the definitions of $R^1$ through $R^9$ are as defined above unless as otherwise indicated. Where the following synthetic schemes result in the formation of novel intermediate compounds, such intermediates are also included within the scope of the present invention.

In the following synthetic schemes it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley & Sons, 1981. The protecting groups may be removed at a convenient subsequent stage by methods well known in the art.

Suitable protecting groups for hydroxyl include those groups well known in the art such as: methylthiomethyl, ethylthiomethyl; trisubstituted silyl such as trimethylsilyl, triethylsilyl, tributylsilyl, tri-i-propylsilyl, t-butyldimethylsilyl, tri-t-butylsilyl, methyldiphenylsilyl, ethyldiphenylsilyl, t-butyldiphenylsilyl, and the like; acyl such as acetyl, pivaloyl, benzoyl, 4-methoxybenzoyl, 4-nitrobenzoyl and aliphatic acyl substituted with aromatic group, which are derived from carboxylic acids; and the like.

Suitable protecting groups for amino include those groups well known in the art which are: benzyl, benzyloxymethyl, benzyloxycarbonyl (carbobenzyloxy), benzylsulfonyl, 2-bromoethyloxycarbonyl, t-butyloxycarbonyl, 2-chlorobenzyloxycarbonyl, 2-chloroethyloxycarbonyl, di-t-amyloxycarbonyl, 9-fluoro-enylmethyloxycarbonyl, isopropoxycarbonyl, 4-methoxybenzyloxycarbonyl, 4-nitrobenzyloxycarbonyl, 2-nitrophenylsulfonyl, phthaloyl, 2,2,2-trichloro-t-butyloxycarbonyl, trifluoroacetyl, triphenylmethane and vinyloxycarbonyl groups and the like in which the preferred ones are the t-butyloxycarbonyl, benxyloxycarbonyl (carbobenzyloxy), 2-chlorobenzyloxycarbonyl, 4-methoxybenzyloxycarbonyl and 4-nitrobenzyloxycarbonyl groups and in which the more preferred ones are the t-butyloxy-carbonyl and the benzyloxycarbonyl (carbobenzyloxy) groups.

The object compounds of Formula I obtained according to the reactions as explained below can be isolated and purified in a conventional manner, for example, extraction, precipitation, fractional crystallization, recrystallization, chromatography, and the like. Because some of the instant compounds may be light-sensitive, it may be necessary to take appropriate precautions in executing manipulations.

Norphysostigmine derivatives (wherein $R^2$ or $R^3$ are hydrogen) and derivatives bearing a hydroxyl group on selected carbon atoms may be prepared by appropriate modifications of the synthetic schemes disclosed by Julian et al., *J. Chem. Soc.*, 563–566 and 755–757 (1935), Yu et al., *Heterocycles*, 27 1709 (1988), U.S. Pat. Nos. 4,791,107, 4,900,748 and 4,983,616 and in U.K. Patent Application 2,005,259.

As illustrated in Reaction Scheme A (wherein $R^2$ and $R^3$ are a secondary amino protecting group or as defined for (I) above, and wherein $R^4$–$R^9$ are a protected hydroxy group or as defined for (I) above and $R^{11}$ is hydrogen or a hydroxy protecting group) various physostigmine derivatives may be prepared.

Starting with an appropriate aniline derivative, the desired oxindole may be prepared by alkylation followed by Freidel Craft cyclization, especially with a Lewis acid such as AlCl₃. Regioisomers, if formed, may be separated by convential techniques.

The oxindole derivative is alkylated with a halogenated acetonitrile (wherein X is Cl, Br or I) to give a mixture of isomers in the presence of inorganic base especially an alkali metal alkonide, such as sodium ethoxide, in an alcoholic solvent, especially a lower alkanol, such as ethanol. This alkylation may also be conducted essentially as described in European Patent Application No. 0,438,796 to give the alkylated oxindole by stereoselective synthesis.

It may be desirable at this step of the synthesis to perform an optical resolution of the isomers. The resolution may be conducted essentially as described by Schonenberger et al., *J. Med. Chem.*, 29, 2268–2273 (1986), and Schonenberger at al., *Helv. Chim. Acta.*, 69, 283–287 and 1486–1497 (1986).

Catalytic hydrogenation of the nitrile in the presence of a palladium or platinum catalyst under an atmosphere of hydrogen in an appropriate solvent gives the corresponding amine.

Cyclization of the amine may be conducted under reductive conditions, preferably using sodium in an aliphatic low molecular weight alcohol, for example methanol or ethanol. After completion of the slow addition of metallic sodium to an alcoholic solution of the amine, the resultant solution is acidified and the solvent is removed under reduced pressure. The solution is basified and the cyclized product is extracted into a suitable organic solvent.

Alkylation of the nitrogen at N-1 is performed by utilizing a strong base, such as sodium hydride, for proton abstraction followed by reaction with a formaldehyde equivalent.

The protecting group on the 5-phenol is then removed, if necessary by standard methods. For example, if the phenol is protected as the methyl ether, treatment with aluminum trichloride or boron tribromide gives the deprotected phenol.

Removal of the protecting group on the 5-phenol is followed by reaction with the desired isocyanate (wherein $R^{10}$ is $R^1$, such as heptylisocyanate) under conditions described in Reaction Scheme E. Removal of any remaining protecting groups, if necessary, gives the compounds of Formula I.

REACTION SCHEME A

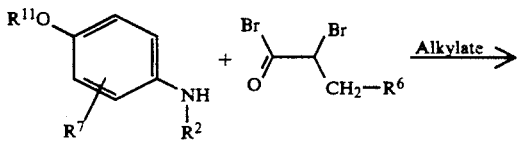

-continued
REACTION SCHEME A

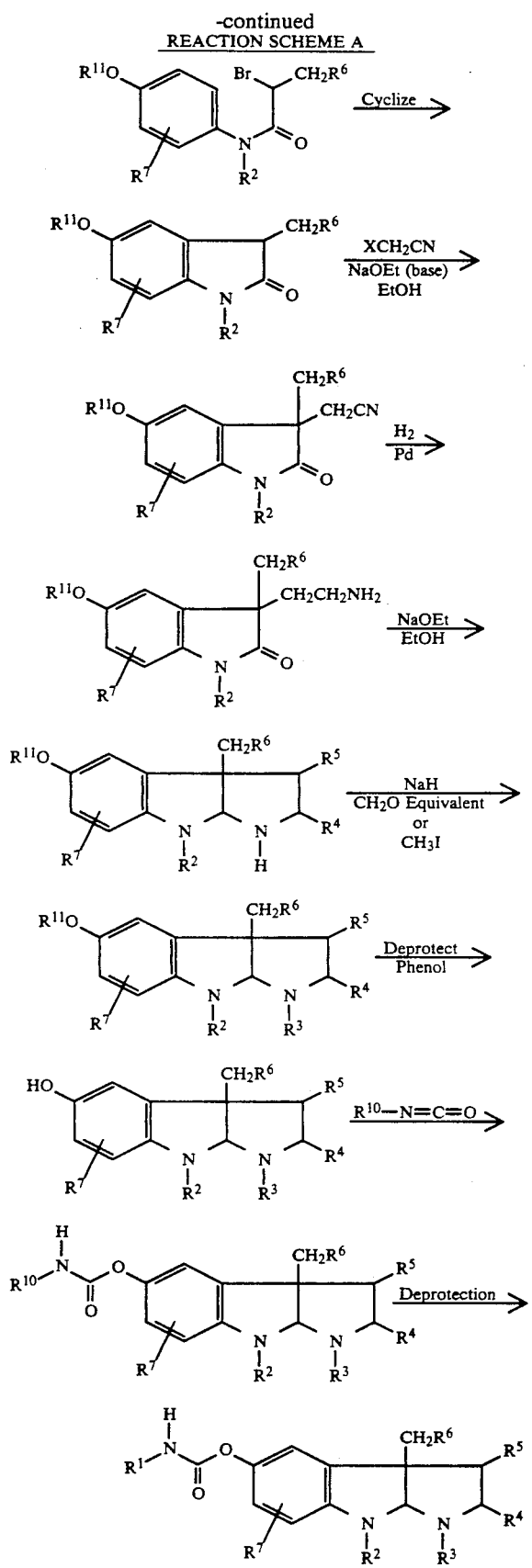

Compounds of Formula I bearing a hydroxy group at C-3 ($R^5$) may also be prepared by Reaction Scheme B.

The starting lactone (prepared essentially by the method of P. Rosenmund and A. Sotiriou, *Angew. Chemie*, 76, 187 (1964)) is reacted with an amine of formula $NH_2R^3$, preferably at a temperature of about 50° C. in a lower alkanol, such as ethanol or methanol. Oxidation of the amide (following enolate formation with a base such as sodium hydride or sodium ethoxide) may be achieved for example by employing a 2-sulfonyloxaziridine, especially 2-phenylsulfonyl-3-phenyloxaziridine. Following protection of the hydroxy group (wherein $R^5$ is protected hydroxy) the amide carbonyl is removed by reduction, especially metal hydride reduction such as with lithium aluminum hydride in an appropriate solvent such as tetrahydrofuran. The resultant compound may be reacted as described in Reaction Scheme E to give the compound bearing a hydroxy group at C-3.

REACTION SCHEME B

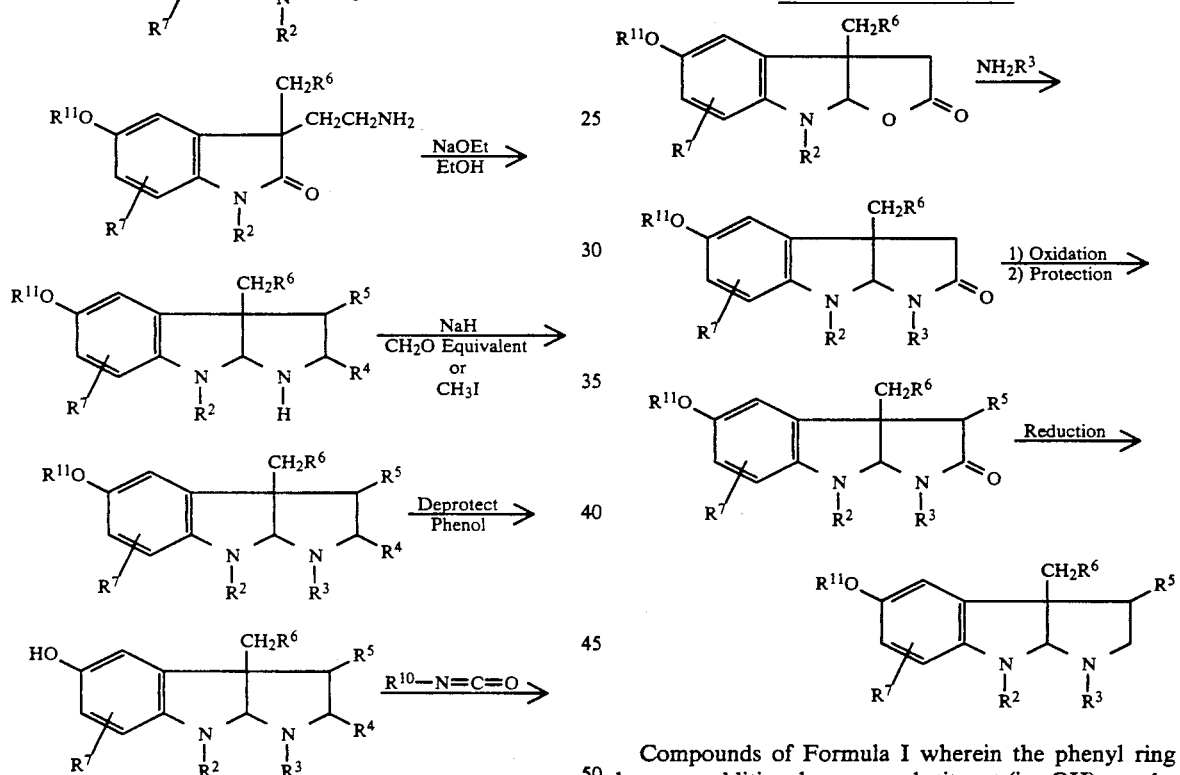

Compounds of Formula I wherein the phenyl ring bears an additional oxygen substituent (i.e. OH) may be prepared by Reaction Scheme C. An appropriate physostigmine derivative (for example heptylphysostigmine or eseroline), wherein $R^{12}$ is hydrogen, or a hydroxy protecting group or is selected from $R^1$, is allowed to react with nitronium tetrafluoroborate (approx. 1.0–1.1 equivalents) in a suitable solvent such as acetonitrile at a temperature of about −50° to 82° C. The nitro group is reduced to the amine by catalytic hydrogenation with a platinum or palladium catalyst such as platinum oxide or palladium on carbon to give the corresponding amine. The aryl diazonium ion is formed by reaction of the amine with nitrous acid or an alyklnitrite under acidic conditions. The diazonium compound is converted to the phenol by hydrolysis in the presence of a copper (II) salt, especially cuprous oxide. Removal of protecting groups, if necessary, gives the desired phenolic compound.

REACTION SCHEME C

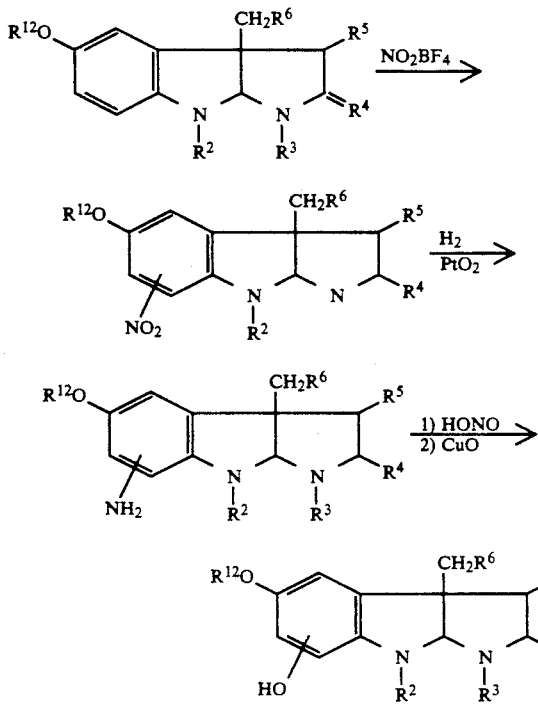

Compounds of Formula I may also be prepared by direct hydroxylation of eseroline or a physostigmine derivative, such as heptylphysostigmine. Appropriate reagents for performing such an oxidation include $H_2O_2$—$SbF_5$, $K_2S_2O_8$—KOH and $FeCl_3$ in the presence of pyrocatechol. Following the oxidation and separation of products, protecting groups are removed, if appropriate, to give the compound of Formula I.

REACTION SCHEME D

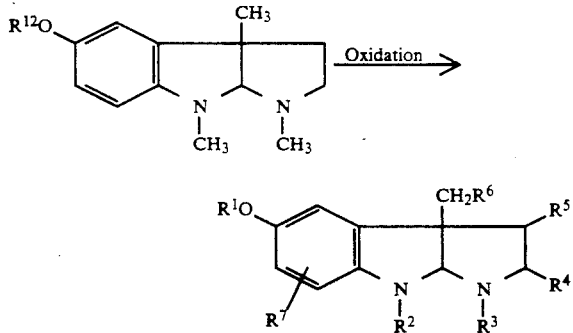

Compounds of Formula I bearing substituents on the alkyl side chain $R^1$ may be prepared by acylation of eseroline (or an eseroline derivative) as depicted in Reaction Scheme E. Eseroline itself may be prepared by hydrolysis of physostigmine as described in U.S. Pat. No. 4,831,155. Eseroline is reacted with an isocyanate of the formula $R^{10}$—N=C=O (wherein $R^{10}$ is $R^1$ bearing a protected hydroxy group or a protected carboxy group) to give the desired physostigmine derivative. In general, eseroline and the appropriate isocyanate are dissolved in a suitable solvent such as anhydrous tetrahydrofuran or benzene which has been previously degassed. The reaction is conducted at a temperature between −50° C. and solvent reflux temperature. The protecting group on the hydroxy or carboxy group is removed by methods well known in the art for the removal of such protecting groups.

REACTION SCHEME E

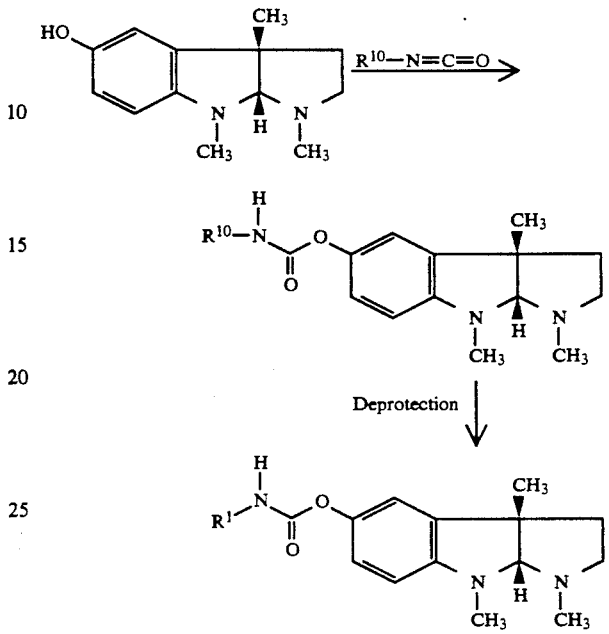

The compounds of Formula I of the present invention are useful for the treatment of various memory dysfunctions characterized by a decreased cholinergic function such as Alzheimer's disease.

This utility is manifested by the ability of these compounds to inhibit cholinesterase enzymes.

The cholinesterase inhibitory activity of either urine or HPLC fractions of urine from a dog to which trimethyl-1,3a,8-hexahydro-1,2,3,3a,8,8a-pyrrol[2,3-b]indole-5(3aS,8aR) heptyl carbamate was administered were determined by a colorimetric assay as described by M. Whittaker (*Methods in Enzymatic Analysis*, Bergmayer and Crassel Eds., Vol. 3, pp. 52-73, 1983) (see Example I and Table I).

Effective quantities of the compounds of the invention may be administered to a patient by any of the various methods, for example, orally as in capsule or tablets, parenterally in the form of sterile solutions or suspension, and in some cases intravenously in the form of sterile solutions. The free base compounds, while effective themselves, may be formulated and administered in the form of their pharmaceutically acceptable acid addition salts for purposes of stability, convenience of crystallization, increased solubility and the like.

The compounds of the present invention are capable of forming acid addition salts with various inorganic and organic acids and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, palmoate, persulfate, picrate, pivalate, propionate, succinate, tartrate, tosylate, and undecanoate. Preferred acid addition salts include the citrate, maleate and tartrate, wherein the tartrate is especially preferred. Salts of the compounds of the present invention may be prepared and employed essentially as described U.S. Pat. No. 4,978,673. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin. In particular, pharmaceutically acceptable salts of the instant compounds may be prepared essentially as described in U.S. Pat. No. 4,978,673.

C. Utility of the compounds within the scope of the invention

The compounds of Formula I may be employed as cholinesterase inhibitors by methods and in dosages known in the prior art for compounds such as trimethyl-1,3a,8-hexahydro-1,2,3,3a,8,8a-pyrrol[2,3-b]indole-5(3aS,8,aR) methylcarbamate, trimethyl-1,3a,8-hexahydro-1,2,3,3a,8,8a-pyrrol[2,3-b]indole-5(3aS,8aR) heptylcarbamate, (3aS-cis)-1,2,3,3a,8,8a-hexahydro-1,3a,8-trimethylpyrrolo[2,3-b]-indol-5-ol, 4-morpholinylcarbamate ester, 3aS-cis-6-bromo-1,2,3,3a,8,8a-hexahydro-1,3a,8-trimethyl-pyrrol[2,3-b]indol-5-ol(1,2,3-trihydroisoquinolyl)carbamate. These compounds possess pharmacological activity such as inhibition of cholinesterase enzymes thereby increasing choline levels in the brain, and therefore are useful for the treatment of senile dementia of the Alzheimer type. In addition, the compounds of Formula I, being cholinesterase inhibitors, have cholinominetic effects in cholinergically-innervated effector organs and are useful in the treatment of glaucoma, myasthenia gravis and paralytic ileus.

The compounds of Formula I are also useful as analgesic agents due to their ability to alleviate pain in mammals.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual nontoxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

The tablets, pills, capsules, troches and the like may also contain the following ingredients: a binder such as micro-crystalline cellulose, gum tragacanth or gelatin; an excipient such as starch or lactose, a disintergrating agent such as alginic acid, Primogel, cornstarch and the like a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating compounds, sucrose as a sweetening agent and certain preservatives, dyes, coloring and flavors. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as asorbic acid or sodium bisulfite; chelating agents such as ethylenediaminetetraacetic acid; buffers such as acetates, cirates or phosphates and agents for the adjustment of tonicity such as sodium chloride or dextrose. The parenteral preparation can be enclosed in disposable syringes or multiple dose vials made of glass or plastic.

For the treatment of these conditions and diseases caused by decreased cholinergic function or for the alleviation of pain a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Dosage levels of the compounds of the present invention are of the order from about 0.01 mg to about 12 mg per kilogram of body weight per day, preferably from about 0.1 mg to about 10 mg per kilogram of body weight per day, are useful in the treatment of the above-indicated conditions (from about 0.7 mg to about 700 mg per patient per day, assuming a 70 kg patient). In addition, the compounds of the present invention may be administered on an intermittent basis; i.e. at daily, semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 500 mg of active agent compounded with an appropriate and convenient amount of carrier material which may vary from about 5 to about 95 percent of the total composition. Dosage unit forms will generally comprise from about 0.1 mg to about 250 mg, and preferably about 0.5 mg to about 100 mg of active ingredient. For parenteral administration the compound of Formula I may be formulated within the range of, for example, 0.01% to 60% by weight, preferably from 0.1 to 20% by weight, and most preferably from about 1.0 to 10% by weight.

It will be understood, however, that the specific dose level for any particular patient will depend on a variety of factors including the activity of the specific compound employed, the age, body weight, general health, gender, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

$^3$H-Heptylphysostigmine (specific activity=4–10 μCi/mg) was administered either orally (1 mg/kg) or intravenously (0.2 mg/kg) to male pure bred beagle dogs (approx. 10 kg body weight). Blood, urine and feces were collected at predetermined time intervals. Assays for heptylphysostigmine in plasma, total radioactivity equivalents in plasma, RBC, urine and feces and cholinesterase activity in plasma and RBC were performed. Aliquots of urine were also assayed for presence of cholinesterase inhibitory material.

Aliquots of filtered urine or plasma extracts were chromatographed on a Spherisorb 5 μm phenyl column (4.6×250 mm) eluted at a flow rate of 1.5 ml/min with a gradient of 5% to 85% acetonitrile in 10 mM sodium acetate, pH 3.5. Eluate was collected in 1 minute fractions and assayed for radioactivity and cholinesterase inhibitory activity.

After drying fractions on a speedvac under reduced pressure, the residue was dissolved in the assay buffer and incubated with control dog plasma at room temperature for 1 hour. To this were added propionylthiocholine and DTNB, the solution was mixed, and the formation of the colored product was monitored at 410 nm every 30 seconds for 2 minutes.

The results of this study are shown in Table I.

TABLE I

| | HPLC FRACTIONATION OF DOG URINE (1 mg/kg P.O.) | |
|---|---|---|
| Fraction # (time in min.) | Radioactivity (DPM) | Cholinesterase (% Inhibition) |
| 1 | 0 | 0 |
| 2 | 3 | 7 |
| 3 | 120 | 20 |
| 4 | 82 | — |
| 5 | 443 | 4 |
| 6 | 134 | — |
| 7 | 89 | 5 |
| 8 | 818 | — |
| 9 | 131 | 17 |
| 10 | 284 | 8 |
| 11 | 213 | 4 |
| 12 | 71 | 3 |
| 13 | 59 | 2 |
| 14 | 69 | 4 |
| 15 | 46 | — |
| 16 | 25 | 4 |
| 17 | 42 | 5 |
| 18 | 241 | 4 |
| 19 | 649 | 23 |
| 20 | 812 | 10 |
| 21 | 300 | 4 |
| 22 | 120 | 9 |
| 23 | 67 | 2 |
| 24 | 66 | 14 |
| 25 | 12 | 3 |

EXAMPLE 2

Incubation of heptylphysostigmine with dog liver microsomes or 9,000×g supernatant fractions was performed to generate metabolites. The incubation mixture contained 100 μmoles of potassium phosphate, pH 7.4, 3 μmoles of MgCl$_2$, 0.5 μmole of NADPH, 1 mg microsomal or 4 mg S9 protein and 10 nmols of $^3$H-heptylphysostigmine in a final volume of 1.0 ml. The incubations were carried out at 37° C. and 120 rpm for 10, 30 or 60 minutes. At the end of the incubation period, metabolites were extracted with a 2:1 mixture of ethyl acetate and acetone. After centrifugation, the organic layer was carefully separated, dried and stored at −20° C. until HPLC analysis. HPLC was carried out as described in Example 1 above except 50 mM ammonium acetate, pH 4.3 was used instead of 10 mM sodium acetate, pH 3.5 and fractions were collected and assayed for cholinesterase inhibitory activity as described in Example 1.

EXAMPLE 3

LC/MS and LC/MS/MS analysis was performed on a Sciex API III tandem mass spectrometer operated under atmospheric pressure chemical ionization mode with heated nebulizer interface for transferring liquid eluate to the ion source.

Aliquots of filtered urine or concentrated extracts of microsomal incubates were run on HPLC under the conditions described in Example 2 above.

The results of these experiments are summarized in Table II.

TABLE II

| Molecular Weight Information Obtained by LC/MS/MS for the Parent Compound and Metabolites | | |
|---|---|---|
| Sample ID | Calculated mol. wt. | Pseudomolecular ion [MH]$^+$ |
| Parent | 359 | 360 |
| Metabolite 1 | 345 | 346 |
| Metabolite 2 | 345 | 346 |
| Metabolite 3 | 361 | 362 |
| Metabolite 4 | 333 | 334 |
| Metabolite 5 | 375 | 376 |
| Metabolite 6 | 375 | 376 |
| Metabolite 7 | 375 | 376 |

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of Formula I:

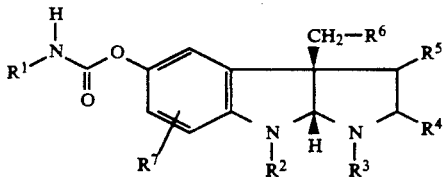

or a pharmaceutically acceptable salt thereof, wherein:
R$^1$ is selected from the group consisting of:
(1) —(CH$_2$)$_6$CH$_3$
(2) —C$_7$H$_{14}$OH,
(3) —(CH$_2$)$_4$—CO$_2$H, and
(4) —(CH$_2$)$_2$—CO$_2$H;
R$^2$ is —CH$_2$R$^8$;
R$^3$ is —CH$_2$R$^9$;

$R^4$, $R^5$, $R^6$, $R^7$, $R^8$ and $R^9$ are independently selected from: hydrogen and hydroxy;

with the proviso that if $R^4$, $R^5$, $R^6$, $R^7$, $R^8$ and $R^9$ are hydrogen, then $R^1$ is other than —(CH$_2$)$_6$CH$_3$.

2. The compound of claim 1 in essentially pure form.

3. The compound of claim 1 wherein the pharmaceutically acceptable salt is selected from the group consisting of: citrate, maleate and tartrate.

4. The compound of claim 1 which is:

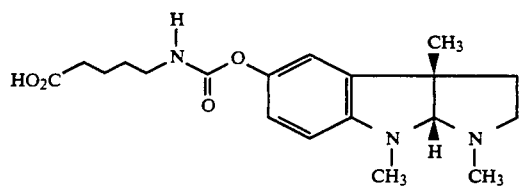

or a pharmaceutically acceptable salt thereof.

5. The compound of claim 4 in essentially pure form.

6. The compound of claim 1 which is:

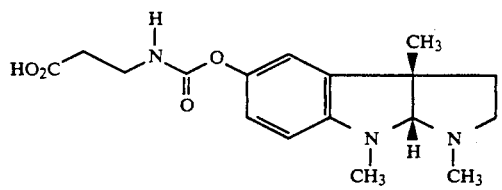

or a pharmaceutically acceptable salt thereof.

7. The compound of claim 6 in essentially pure form.

8. The compound of claim 1 which is:

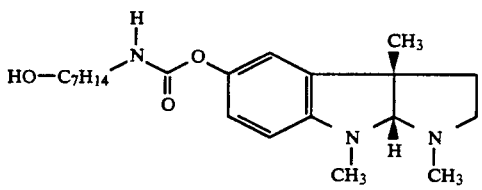

or a pharmaceutically acceptable salt thereof.

9. The compound of claim 8 in essentially pure form.

10. The compound of claim 1 which is:

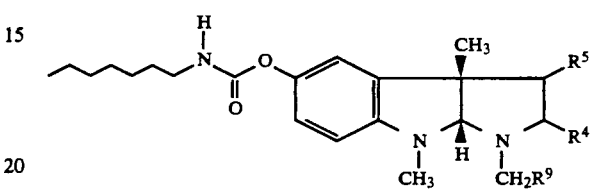

or a pharmaceutically acceptable salt thereof, wherein $R^4$, $R^5$ and $R^9$ are independently selected from: hydrogen and hydroxy, with the proviso that one of $R^4$, $R^5$ and $R^9$ is hydroxy and the remaining two are hydrogen.

11. The compound of claim 10 in essentially pure form.

12. The compound of claim 1 which is:

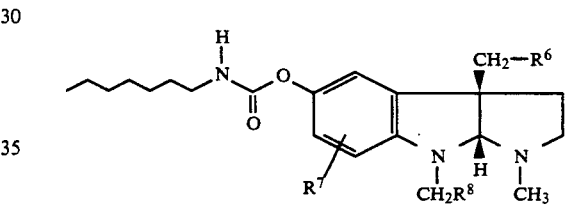

or a pharmaceutically acceptable salt thereof, wherein $R^6$, $R^7$ and $R^8$ are independently selected from: hydrogen and hydroxy, with the proviso that one of $R^6$, $R^7$ and $R^8$ is hydroxy and the remaining two are hydrogen.

13. The compound of claim 12 in essentially pure form.

14. A pharmaceutical composition comprising the compound of claim 1 and a suitable carrier therefor.

15. A method of treating a patient in need of cholinesterase inhibition which comprises administering to the patient a cholinesterase inhibiting effective amount of the compound of claim 1.

* * * * *